US00PP18643P2

(12) United States Plant Patent
Oudshoorn

(10) Patent No.: US PP18,643 P2
(45) Date of Patent: Mar. 25, 2008

(54) ***PAPAVER* PLANT NAMED 'WHITE RUFFLES'**

(50) Latin Name: *Papaver orientale*
Varietal Denomination: White Ruffles

(75) Inventor: Hubertus Gerardus Oudshoorn, Rijpwetering (NL)

(73) Assignee: Future Plants Licantie B.V., Lisserbroek (NL)

( * ) Notice: Subject to any disclaimer, the term of this patent is extended or adjusted under 35 U.S.C. 154(b) by 0 days.

(21) Appl. No.: 11/520,893

(22) Filed: Sep. 14, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Papaver* plant named 'White Ruffles', characterized by its upright and compact plant habit; moderately vigorous growth habit; and flowers with ruffled white-colored petals.

2 Drawing Sheets

Botanical designation: *Papaver orientale.*
Cultivar denomination: 'White Ruffles'.

BACKGROUND OF THE INVENTION

The present invention relates to a new and distinct cultivar of *Papaver,* botanically known as *Papaver orientale* and hereinafter referred to by the name 'White Ruffles'.

The new *Papaver* originated from an open-pollination in 2001 of an unnamed selection of *Papaver orientale,* not patented, as the female, or seed, parent with an unknown selection of *Papaver orientale,* as the male, or pollen, parent. The new *Papaver* was discovered and selected by the Inventor as a single flowering plant from within the progeny of the stated open-pollination grown in a controlled environment in Rijpwetering Wetering, The Netherlands in 2005.

Asexual reproduction of the new cultivar by divisions in Rijpwetering, The Netherlands has shown that the unique features of this new *Papaver* are stable and reproduced true to type in successive generations.

SUMMARY OF THE INVENTION

Plants of the cultivar White Ruffles have not been observed under all possible environmental conditions. The phenotype may vary somewhat with variations in environment such as temperature and light intensity without, however, any variance in genotype.

The following traits have been repeatedly observed and are determined to be the unique characteristics of 'White Ruffles'. These characteristics in combination distinguish 'White Ruffles' as a new and distinct cultivar of *Papaver:*

1. Upright and relatively compact plant habit.
2. Moderate vigorous growth habit.
3. Flowers with ruffled white-colored petals.

Plants of the cultivar White Ruffles differ from plants of the parent selections in plant height as plants of the new *Papaver* are more compact than plants of the parent selections.

Plants of the new *Papaver* can be compared to plants of the cultivar Pink Ruffles, disclosed in U.S. Plant Pat. No. 12,712. In side-by-side comparisons conducted in Rijpwetering, The Netherlands, plants of the new *Papaver* differed from plants of the cultivar Pink Ruffles in the following characteristics:

1. Plants of the new *Papaver* were more compact than plants of the cultivar Pink Ruffles.
2. Plants of the new *Papaver* and the cultivar Pink Ruffles differed in flower color as plants of the new cultivar Pink Ruffles had pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Papaver.*

The photograph on the first sheet is a side perspective view of typical plants of 'White Ruffles' grown in an outdoor nursery.

The photograph at the top of the second sheet is a close-up view of a typical flower of 'White Ruffles'.

The photograph at the bottom of the second sheet is a close-up view of a typical leaf of 'White Ruffles'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the late spring/early summer in an outdoor nursery in Rijpwetering, The Netherlands for about one year. During the production of the plants, day temperatures ranged from 14° C. to 27° C. and night temperatures ranged from 5° C. to 14° C.

Botanical classification: *Papaver orientale* cultivar White Ruffles.

Parentage:

*Female parent.*—Unnamed selection of *Papaver orientale,* not patented.

*Male parent.*—Unknown selection of *Papaver orientale,* not patented.

Propagation:

*Type.*—By divisions.

*Root description.*—Thick, fleshy; light brown in color.

Plant description:

*Form.*—Herbaceous perennial flowering plant; compact; mostly upright; columnar. Basally branching, rosette; flowering stems arise from the base. Moderately vigorous growth habit.

*1. Plant height.*—About 41 cm.

*Plant width.*—About 42 cm.

*Branch description.*—Arrangement: Basal branching; about two basal branches develop per plant. Length: About 36.4 cm. Diameter: About 5 mm. Internode length: About 6.4 cm. Strength: Strong. Aspect: Upright. Texture: Pubescent; rough. Color: 144A to 144B.

Foliage description:

*Arrangement.*—Alternate, simple.

*Length.*—About 28.2 cm.

*Width.*—About 6.2 cm.

*Shape.*—Pinnatifid to pinnatisect.

*Apex.*—Broadly acute.

*Base.*—Cuneate.

*Margin.*—Serrate or doubly serrate.

*Texture, upper and lower surfaces.*—Pubescent; rough.

*Venation pattern.*—Pinnate.

*Color.*—Developing foliage, upper surface: 143A to 144A. Developing foliage, lower surface: 138A. Fully expanded foliage, upper surface: 141A; venation, 145D. Fully expanded foliage, lower surface: 137B; venation, 144B to 144C.

*Petiole length.*—About 11.4 cm.

*Petiole diameter.*—About 6 mm.

*Petiole color, upper and lower surfaces.*—144B.

Flower description:

*Flower arrangement and appearance.*—Large single rotate flowers; flowers terminal and face mostly upright; about two flowers per plant at one time.

*Natural flowering season.*—Continuous flowering from late May to late June in The Netherlands.

*Flower longevity on the plant.*—About three days; flowers not persistent.

*Fragrance.*—None detected.

*Flower buds.*—Length: About 3.6 cm. Diameter: About 2.7 cm. Shape: Broadly ovate. Texture: Densely pubescent. Color: 137A.

*Flower diameter.*—About 9.4 cm.

*Flower depth (height).*—About 4.6 cm.

*Petals.*—Arrangement: About five in a single whorls. Length: About 7.1 cm. Width: About 6.5 cm. Shape: Roughly flabellate. Apex: Irregular, deeply incised; ruffled in appearance. Margin: Entire. Texture, upper and lower surfaces: Smooth, glabrous. Color: When opening and fully opened, upper surface: 155C; towards the base, 187C; central black spot, between N186C and 202A. When opening and fully opened, lower surface: 155C; towards the base, 187C; venation, between N186C and 202A.

*Sepals.*—Arrangement: About two in a single whorl. Length: About 1.7 cm. Width: About 2 cm. Shape: Pinnatisect. Apex: Acute. Margin: Serrate. Texture, upper and lower surfaces: Densely pubescent. Color, upper surface: 141B. Color, lower surface: 141A.

*Peduncles.*—Length: About 36.4 cm. Diameter: About 5 mm. Strength: Strong. Texture: Pubescent; rough. Color: 144A to 144B.

*Reproductive organs.*—Stamens: Quantity per flower: About 250. Filament length: About 2.2 cm. Filament color: 202A; towards the base, 187A. Anther shape: Oblong. Anther length: About 2.5 mm. Anther color: 202A. Pollen amount: Scarce. Pollen color: N186A to 202A. Pistils: Quantity per flower: About twelve. Pistil length: About 8 mm. Stigma shape: Narrowly oblong. Stigma color: N186B. Ovary color: 138A to 138B.

*Fruits.*—Type: Capsule. Quantity per flower: One. Length: About 2.1 cm. Diameter: About 1.9 cm. Color: 137A.

*Seeds.*—Quantity per fruit: About 750. Length: About 1 mm. Diameter: About 1 mm. Color: 202A to 202B.

Disease/pest resistance: Plants of the new *Papaver* have not been noted to be resistant to pathogens and pests common to *Papaver.*

Garden performance: Plants of the new *Papaver* have exhibited good tolerance to rain, wind, high temperatures of 30° C. and are hardy to USDA Zone 4.

It is claimed:

1. A new and distinct *Papaver* plant named 'White Ruffles' as illustrated and described.

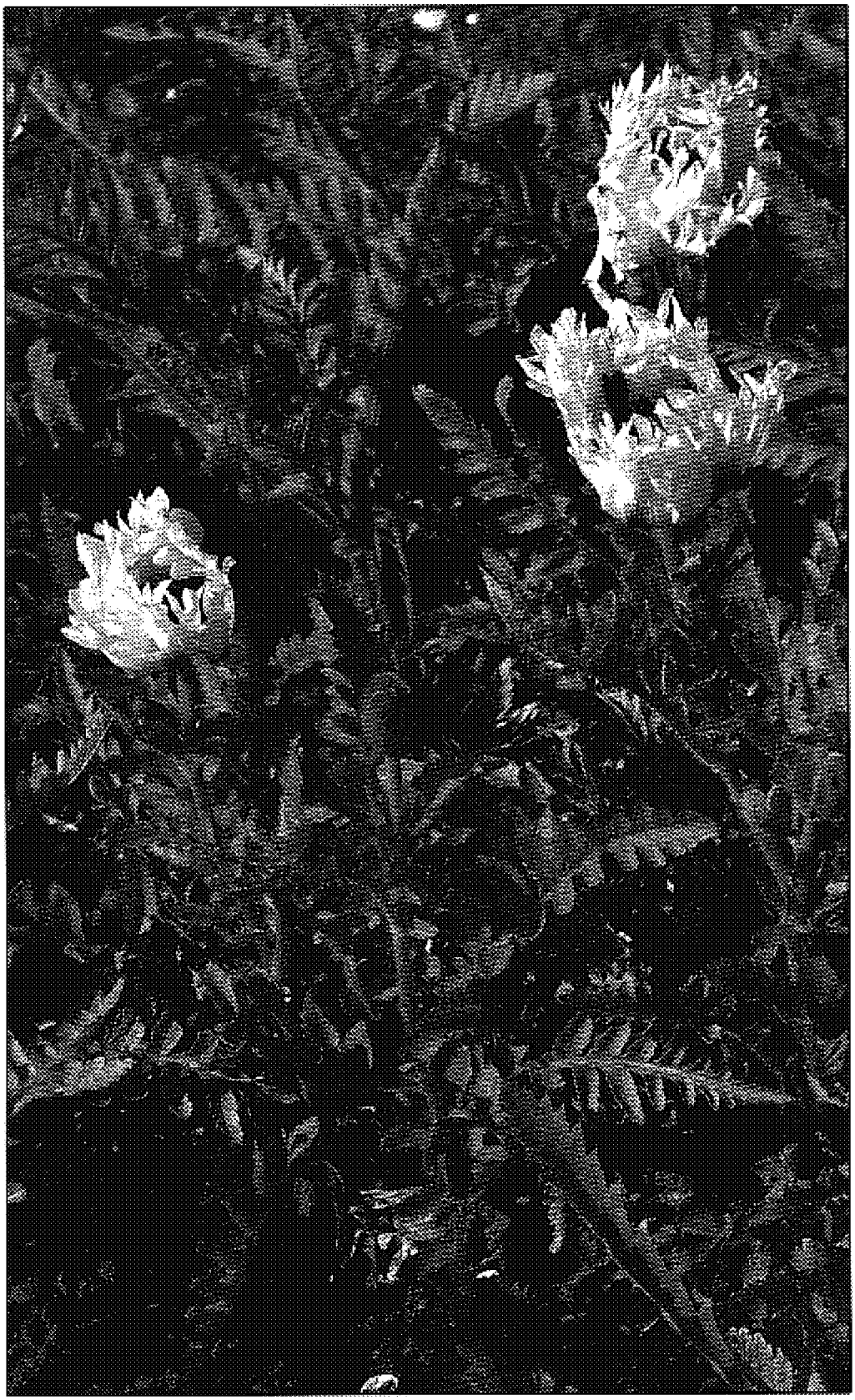

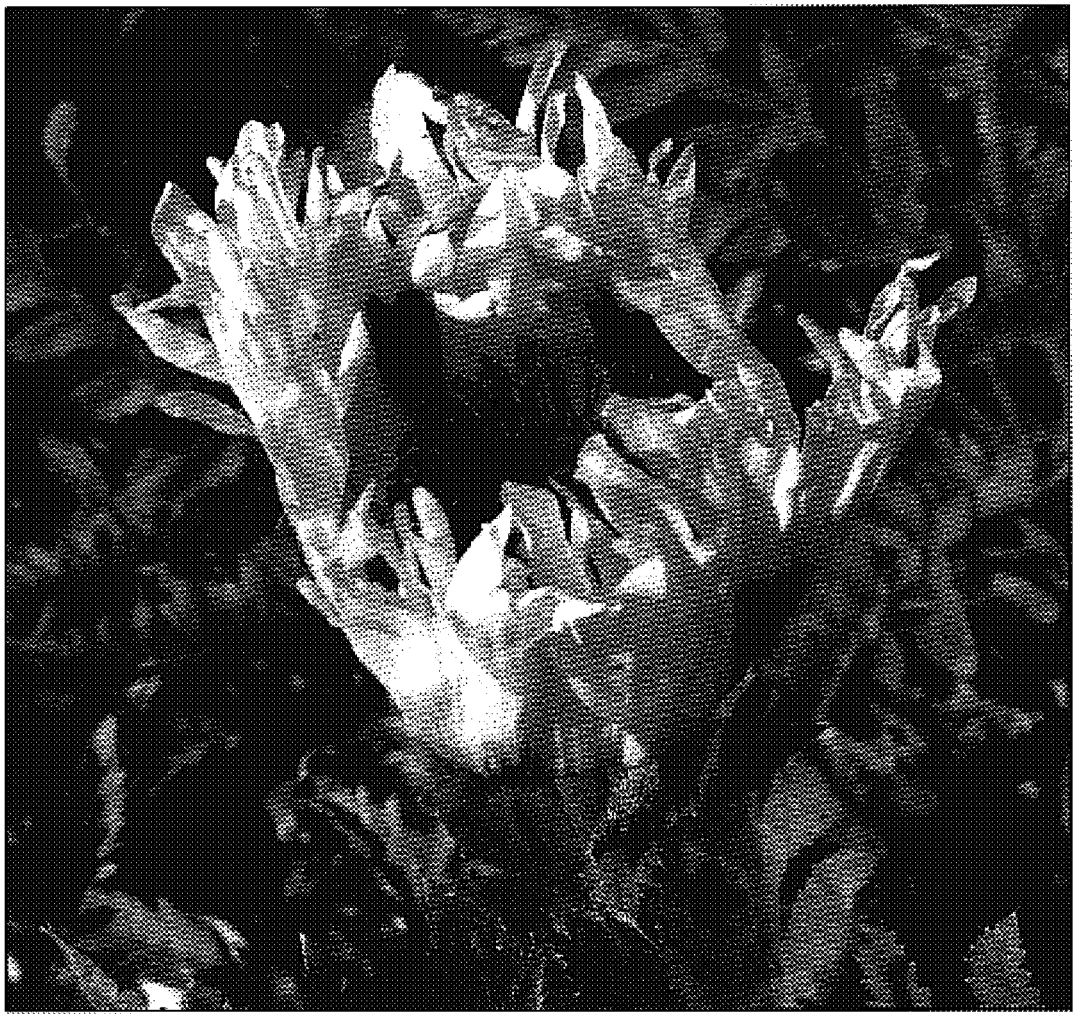
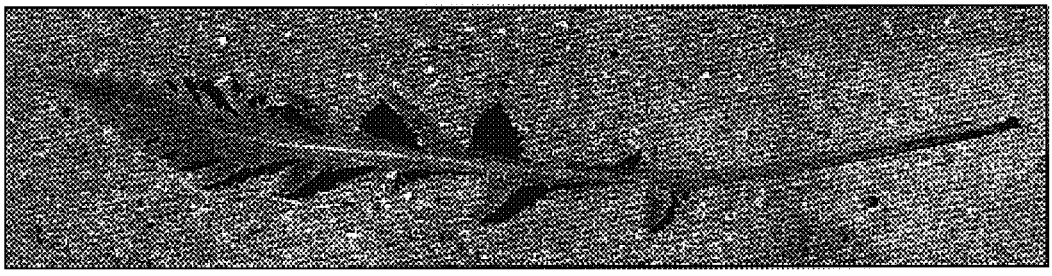

* * * * *